United States Patent [19]

Lehmann et al.

[11] 4,412,000

[45] Oct. 25, 1983

[54] METHOD OF BINDING A BIOLOGICALLY ACTIVE MATERIAL TO A CARRIER CONTAINING HYDROXYL GROUPS

[75] Inventors: Hans-Dieter Lehmann; Gerd G. Krisam, both of Hechingen; Ruth S. Golla, Hechingen-Weilheim, all of Fed. Rep. of Germany

[73] Assignee: Gambro Dialysatoren KG, Fed. Rep. of Germany

[21] Appl. No.: 320,215

[22] Filed: Nov. 12, 1981

[30] Foreign Application Priority Data

Nov. 19, 1980 [SE] Sweden .............................. 8008096

[51] Int. Cl.³ ...................... C12N 11/12; C12N 11/08; C12N 11/06

[52] U.S. Cl. ................................... 435/179; 435/180; 435/181

[58] Field of Search ............... 435/174, 178, 179, 180, 435/181, 182

[56] References Cited

U.S. PATENT DOCUMENTS 3,841,969 10/1974 Emery et al. .................. 435/179 X
4,177,038 12/1979 Biebricher et al. ............. 435/178 X

OTHER PUBLICATIONS

Chen, et al., Physical Characteristics of Porous Cellulose Beads as Supporting Material for Immobilized Enzymes. Biotech. and Bioeng. vol. XVIII, 1976 (pp. 1507–1516).
Reichelt et al., Uber die Umsetzung von Cellulose und Lignin mit Isocyanaten bzw. isocyanatgruppenhaltigen Prapolymeren, Acta Polymerica, vol. 32, 1981 (pp. 172–176).
Zaborsky, O., Immobilized Enzymes CRC Press Cleveland, Ohio 1973 (pp. 21–22).
Axen, et al., Chemical Fixation of Enzymes to Cyanogen Halide Activated Polysaccharide Carriers, Eur. J. Biochem. vol. 18, 1971 (pp. 351–360).
Jackson, et al., A New Extracorporeal Reactor-Dialyzer for Enzyme therapy Using Immobilized Asparaginase, The Journal of Pharm. and Exp. Therapeutics vol. 209, No. 2, 1979 (pp. 271–274).
Pommerening et al., Problems of Matrix Activation in Using The cyanogen Bromide Method, Journal of Polymer Science; Polymer Symposium, vol. 66, 1979 (pp. 185–188).
Lesiak et al., Chemistry and Application of Organic Isocyanates IV. Die Angewandte Makromolekulare Chemie, vol. 88, 1980 (pp. 179–191).

Primary Examiner—David M. Naff
Attorney, Agent, or Firm—Lerner, David, Littenberg, Krumholz & Mentlik

[57] ABSTRACT

Biologically active material such as an enzyme is bonded to a carrier containing hydroxyl groups by binding an isocyanate compound to the carrier and bonding the biologically active material to the bound isocyanate compound. Binding of the isocyanate compound to the carrier is achieved with the use of a non-toxic titanium based compound which catalyzes the formation of urethane bonds. The preferred non-toxic based titanium compound is an orthotitanium acid ester such as tetrabutyltitanate.

13 Claims, No Drawings

METHOD OF BINDING A BIOLOGICALLY ACTIVE MATERIAL TO A CARRIER CONTAINING HYDROXYL GROUPS

BACKGROUND OF THE INVENTION

1. Field of the Invention

This invention relates to a method of binding a biologically active material, e.g. a protein to a carrier containing hydroxyl groups, wherein an isocyanate compound is bound to the carrier and whereafter the said biologically active material is bound to the so bound isocyanate compound.

2. Background of the Invention

For several inherent reasons it has been necessary to use special methods for binding enzymes to a carrier. One reason is that enzymes are sensitive substances and easily deactivated, requiring the use of mild reaction conditions for the binding. Hydroxyl groups on polymeric materials are very inert and must be attacked by rather aggressive reagents to be used as anchoring groups. Of course, only very strongly reactive groups can therefore take part in the binding reaction. Enzymes to be bound are usually handled in the form of buffered dilute aqueous solutions. This entails the risk that such anchoring groups may be consumed by side-reactions with the large excess of water present.

According to the prior art techniques, some compensation had to be found for such an inherently low reaction efficiency. Particularly, in connection with carriers containing hydroxyl groups, for example polysaccharides, this has been achieved by means of some form of activation of the hydroxyl groups. The most common form for activating has been by means of cyanogen bromide, as described in Axen, Ernback: *European J. Biochem.* 1971, Vol. 18, p. 351.

Although such activating has made it possible to solve the above-mentioned problem, the Axen-type method has entailed other serious disadvantages and risks. As is apparent from scheme 2 in the Axen et al. reference, the bonds are not very stable. The ligands can be split from the carrier, either hydrolytically or especially ammonolytically.

Moreover, contaminating cyanide ions from the cyanogen bromide can affect the activity of some enzymes by blocking central metal atoms. See, for example, K. Pommerening et al., *J. Pol. Sci.: Polymer Symp.*, Vol. 66, pp. 185–188 (1979).

Furthermore, cyanogen halogenides are highly toxic and comparable with hydrocyanic acid in this respect. The use of the strongly toxic and highly volatile (b.p. 61° C.) cyanogen bromide according to the prior art technique therefore requires special measures for safety, especially when being used in industrial quantities.

For steric reasons, some enzymes also require an anchorage to the carrier via a long-chain linkage ("spacer"). In order to provide such an anchorage according to the known BrCN-method, it has therefore been necessary to employ a separate second reaction step, i.e., first to bind a spacer and finally to bind the biologically active material to this spacer.

Finally, the BrCN-method, when used in connection with cellulose-type carriers, has required that the cellulose has firstly been exposed to an alkaline treatment, i.e., mercerizing. See, for example, J. A. Jackson et al., *J. Pharm. +Exp. Therapeutics,* Vol. 209, 2 (1979), p. 271.

Another technique for binding proteins to a carrier is disclosed in Biebricher et al. U.S. Pat. No. 4,177,038. In the Biebricher et al. method, a vehicle containing free —NH$_2$ or —OH groups is reacted under anhydrous conditions with an excess of organic diisocyanate in the presence of a strong basic catalyst to produce vehicle substance which can be reacted with biologically active matter, e.g., protein. The only specific catalyst mentioned is sodium imidazolide. Biebricher et al. also suggest the use of a "spacer" compound.

SUMMARY OF THE INVENTION

It has now been found that a biologically active material, e.g. a protein can be bound to a carrier by a method comprising the steps of binding an isocyanate compound to the carrier in the presence of a non-toxic titanium based compound catalyzing the formation of urethane bonds such as tetrabutyl titanate (TBT), and binding a biologically active material, e.g. a protein to the bound isocyanate compound. This method provides a urethane bond stable against hydrolysis or ammonolysis. By choosing a non-toxic catalyst, the toxic risks, which are unavoidable in connection with the known BrCN-method, are avoided. Moreover, safety risks due to the toxicity of isocyanate compounds (e.g. of Toluene-diisocyanate TDI) are avoided by employing a high boiling isocyanate or a non-volatile isocyanate prepolymer. Furthermore, cyanide ions are not present and mercerization of the carrier is not necessary for this method. A further advantage is that due to the properly chosen length of the isocyanate or isocyanate prepolymer a separate spacer grafting step is not necessary.

The method according to the present invention is useful in several different connections where it is desired to bind a biologically active compound such as a protein or Heparin to a carrier containing hydroxyl groups. The present invention is especially useful in binding the enzyme urease to a carrier on the basis of cellulose for use in connection with extracorporeal treatment of body liquids for hydrolysis of urea in, for example, dialysis of blood.

DETAILED DESCRIPTION OF THE INVENTION

According to the present invention, there is provided a method of binding a biologically active material to a carrier containing hydroxyl groups. The method comprises the steps of binding an isocyanate compound to the carrier in the presence of a non-toxic titanium based compound catalyzing the formation of urethane bonds such as tetrabutyltitanate (TBT), and binding a biologically active material, e.g. a protein to the so bound isocyanate compound. The method provides a catalytic formation of a stable bond by the addition of the isocyanate group to nucleophiles, especially of the formation of a urethane group. Also, since the catalysts are non-toxic, the above-mentioned risks in connection with the known BrCN-method are completely eliminated.

Examples of the non-toxic titanium based catalysts suitable for use in the present invention are orthotitanium acid esters, for example, tetrabutyltitanate. (NIOSH: Registry of toxic effects of chemical substances 1977, Vol. II, p. 912, TXDS (oral rat: LD$_{50}$3122 mg/kg). The esters are preferably low molecular weight alkyl esters, e.g., the esters can contain methyl, ethyl, n-propyl, iso-propyl, or n-butyl groups and isomers and mixtures thereof.

Preferably, the orthotitanium acid ester is used in dissolved form in a low boiling solvent. Suitable solvents include, for example, ether, acetone, dichloromethane or frigen.

The choice of isocyanate compound according to the invention may vary and is dependent on the steric characteristic of the biologically active material to be bound. The isocyanate compound preferably contains at least two isocyanate groups. As desired, the choice can be made among long-chain and short-chain isocyanate compounds depending on the distance from the surface of carrier that is the most suitable for the biologically active material to be bound. For example, such isocyanate compounds may be diisocyanates, triisocyanates, or polyisocyanates with increasing numbers of carbons depending on the required increasing distance. Typical examples of isocyanate compounds according to the invention are diisocyanates as hexymethylene diisocyanate, trimethylhexamethylene diisocyanate, toluene diisocyanate (TDI) or methylene diphenyl diisocyanate (MDI) etc. and triisocyanates as given by the following formulae:

diisocyanate: OCN-A-NCO and
triisocyanate: (OCN-A-)₃Y wherein A is, for example,

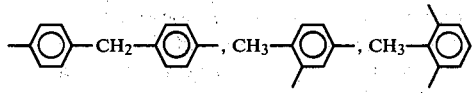

—(CH₂)$_n$—;   —CH₂—C(CH₃)₂—CH₂—CH(CH₃)—CH₂—CH₂—, or

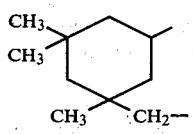

wherein n=2 to 18, preferably 6,

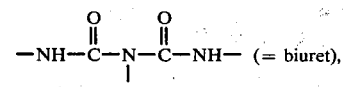  (= biuret),

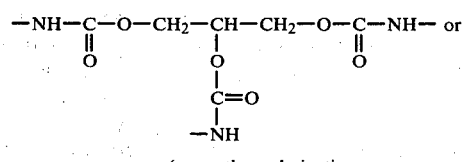

(= urethane derivatives of glycerole or hydroxymethyl groups containing polyoles)

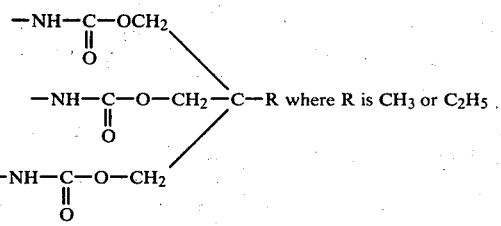

Suitable isocyanate prepolymers include, for example, prepolymers derived from aromatic or aliphatic diisocyanates with diols and triols, such as ethylene glyol, glycerol, trishydroxymethyl ethane, trishydroxymethyl propane, or higher polyols such as sugars, sorbitol, etc.; and biurets derived from diisocyanates, such as methane diphenyl diisocyanate (MDI), toluene diisocyanate (TDI), isophorone-diisocyanate, and the like. The aliphatic isocyanate compounds and the polyisocyanates derived therefrom are preferred. With the aliphatic isocyanate compounds, deactivation of reactive groups for sensitive materials is not required. The aliphatic isocyanate compounds are "selective" because the catalyst will be destroyed rapidly by water. "Selective" means that, in the competition of water and the amino groups of the biologically active material in the reaction with the isocyanate groups of the isocyanate compound grafted to the matrix or carrier, the amino groups preferentially react. Also, the aliphatic isocyanate compounds have a high boiling point and low toxicity. A preferred triisocyanate is N, N', N''tris(6-isocyanatohexyl)biuret, as described by T. Lesiak, et al., *Die Angewandte Makromolekulare Chemie*, Vol. 88, No. 179 (1980).

Preferably, the isocyanate compound is used in dissolved form in an aprotic solvent. Suitable solvents include dichloromethane, acetone, ether or frigen. The isocyanate solution may be added either alone or in combination with a solution of the catalyzing agent according to the invention.

The choice of carrier containing hydroxyl groups may also vary within wide limits. Conveniently, the carrier is selected from polysaccharides, for example, such as cellulose, starch, dextranes and alginates, preferably cellulose. Also, other types of carriers may be used, such as proteins, e.g., collagen, and synthetic polymers, e.g., polyvinyl alcohol, saponified ethylene-vinyl acetate copolymer (ethylene-vinylalcohol copolymer) or hydroxyethylmethacrylate (HEMA). Also, mixtures of carriers or multilayered structures are suitable, e.g., hydroxylic groups containing surface coatings.

Biologically active materials which can be bound to a carrier in accordance with the present invention must have nucleophilic groups able to react with a isocyanate group. Therefore, amino-, hydroxyl- or thiol-groups must be accessable on the biologically active material to be bound. Examples of such materials may be enzymes such as urease etc., co-factors, immunoglobulins, Fc-part of immunoglobulins, certain surface receptors from bacteria having affinity to the Fc-part (for example protein A of Staph. aureus), lectines, glycoproteins and heparin.

The chemical binding mechanisms of the triisocyanate and polyisocyanate compounds can proceed two ways, e.g., as shown below:

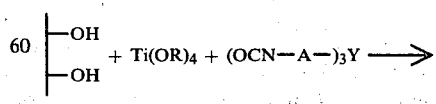

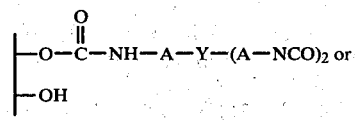

-continued

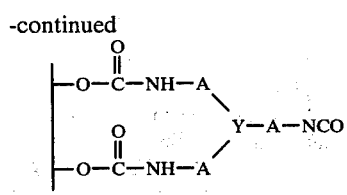

This reaction is conducted in a water-free medium. When water vapor is later contacted with this isocyanate carrier, the catalyst residues not rinsed away in the process are hydrolyzed very rapid, i.e., more rapidly than hydrolysis of the isocyanate groups occurs. Aliphatic isocyanate compounds are not very sensitive to hydrolysis as compared to the catalyst, which becomes desactivated according to:

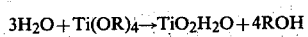

The activated carrier needs no catalyst for the reaction in aqueous solution with the biologically active material or other substances containing nucleophilic groups such as $NH_2$, OH or SH. The reaction products between the biologically active compound and activated carrier can be illustrated as follows:

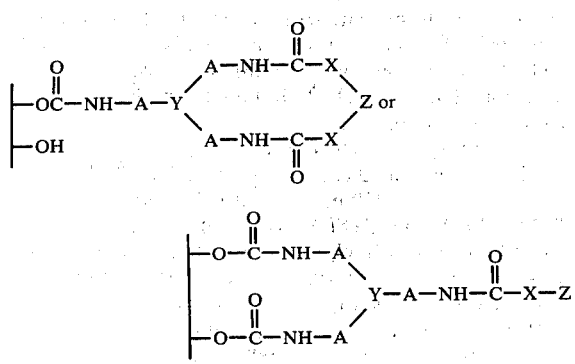

where X is the —NH—, —O—, —S— linkage from the biologically active compound or nucleophilic compound and Z represents the remainder of the protein or nucleophilic compound. Of course, the protein or nucleophilic compound can react with other activated portions of an activated carrier also. The bound biologically active materials are useful in several fields for analysis, synthesis or separation purposes in technical, biological and medical fields. The bound enzyme urease is particularly useful in connection with the extracorporeal treatment of body liquids, for example, for hydrolyzing urea in dialysate of hemodialysis or hemofiltrate.

The invention is illustrated in the examples with especial reference to a method of binding the enzyme urease and albumin as examples of useful biologically active materials according to the invention. This should however, not constitute any restriction of the more general applicability of the present invention as regards the choice of biologically active materials to be bound.

EXAMPLE 1

In this example, cellulose is used in the form of Cuprophan ®-hollow fibers, contained in a Gambro ® Lundia ® fiber dialyzer, as a carrier for urease.

Four separate experiments to bind an isocyanate compound to the carrier were performed with the use of tetrabutyltitanate (TBT) as catalyst for urethane-forming and with the use of hexamethylene diisocyanate N,N',N''-tris(6-isocyanatohexyl)biuret as example of an isocyanate compound.

EXPERIMENT 1

150 ml of a TBT-solution containing 1 g TBT per 200 ml ether were recirculated (50 ml/min) through said Cuprophan ®-hollow fibers for impregnating of the innerwalls of said fibers for 5 minutes. The first 50 milliliters were discarded, followed by rinsing with 100 ml of a rinsing solution (280 ml ether+130 ml dichloromethane).

20 g of said isocyanate compound in 400 ml solvent (280 ml ether+130 ml dichloromethane) were recirculated (50 ml/min) through the so rinsed hollow fibers for 5 minutes to bind said isocyanate to the so impregnated innerwalls of said fibers, whereafter the fibers were rinsed with 200 ml of the above-mentioned rinsing solution.

EXPERIMENT 2

The procedure of Experiment 1 was repeated, but with recirculation of said isocyanate solution for 10 minutes.

EXPERIMENT 3

150 ml of a TBT-solution containing 2 g TBT/200 ml frigen were recirculated (50 ml/min) through said Cuprophan ®-hollow fibers for impregnation of the innerwalls of said fibers for 5 minutes. The first 50 milliliters were discarded.

40 g isocyanate compound in 330 ml solvent (200 ml frigen+130 ml di chloromethane) were recirculated (50 ml/min) through the so impregnated Cuprophan ®-hollow fibers for 10 minutes to bind said diisocyanate to the innerwalls of said fibers, followed by rinsing with 200 ml of a rinsing solution (200 ml frigen+130 ml $CH_2Cl_2$).

EXPERIMENT 4

The procedure of Experiment 3 was repeated, but with 10 minutes impregnating with said TBT-solution and with 20 minutes recirculating of said triisocyanate solution.

Following binding of said triisocyanate according to Experiments 1-4 and rinsing with the respective solvents, said dialyzers were dried under vacuum for 1 hour in a desiccator. Then the enzyme urease (Boehringer 174 882) was bound to the so bound triisocyanate according to the following procedure:

A. Single pass (dialyzers from Experiments 1 and 2).

3000-5000 U of urease in 250 ml phosphate buffer (pH=7) was pumped (10 ml/min) through the above-mentioned triisocyanate-treated dialyzers prepared according to Experiments 1 and 2 to bind the urease to said triisocyanate. The respective end solutions were collected. Determinations of activity were performed according to H. U. Bergmeier, *Methoden der enzymatischen Analyse*, Vol. 1, (1974), on the original as well as the collected urease solutions. The volume of the end solutions was restored prior to determination of activity to the original volume of 150 ml by collecting of the first milliliters of a phosphate buffer solution (pH=7) which was flushed through said dialyzers. (The loss of volume was due to swelling of the Cuprophan ®-hollow fibers). The results are given in Table 1 below.

B. Recirculating (dialyzers from Experiments 3 and 4).

3000–5000 U of urease in 250 ml phosphate buffer (pH=7) was recirculated (10 ml/min) for 1 hour through the above-mentioned triisocyanate-treated dialyzers prepared according to Experiments 3 and 4 to bind said urease to said triisocyanate. Again determinations of activity were performed. The results are given in Table 1 below.

Finally, the activity of the bound urease according to the Berthelot-method was performed in the following way:

18 liters of dialysate, initial concentration of urea about 250 mg%, was pumped (100 ml/min, single pass) through the respective dialyzers. Samples were taken from the respective end solutions after 3 hours for determination of urease. The results are given in Table 1 below.

TABLE 1

| Experiment | Pretreatment with TBT | Pretreatment with triisocyanate | Solvent | Manner of urease binding | Conversion of urea mg, 3h |
|---|---|---|---|---|---|
| 1 | 0.5% 5 min | 5% 5 min | ether ether/CH$_2$Cl$_2$ | single pass | 587 |
| 2 | 0.5% 5 min | 5% 10 min | ether ether/CH$_2$Cl$_2$ | single pass | 684 |
| 3 | 1% 5 min | 12% 10 min | frigen frigen/CH$_2$Cl$_2$ | recirculating | 450 |
| 4 | 1% 10 min | 12% 20 min | frigen frigen/CH$_2$Cl$_2$ | recirculating | 906 |

From Table 1, it is apparent that the activity of the bound urease (as reflected through the conversion of urea) was doubled by doubling of the time for influence of TBT and triisocyanate, compare Experiments 3 and 4.

Consequently, the Example shows that a relatively high activity of the bound urease (900 mg urea is hydrolysed within 3 hours) may be obtained by means of the method according to the present invention.

EXAMPLE 2

In this Example, cellulose is used in the form of Cuprophan ®-wastes from a Gambro ®Lundia ®High-flux dialyzer as a carrier for urease. Said Cuprophan ®-waste had a surface area of about 200 cm$^2$/g.

Twenty-seven different experiments to bind an isocyanate compound to the carrier were performed with the use of TBT as catalyst for urethane-forming and with N,N',N''-tris(6-isocyanatohexyl)biuret(experiments 5–25) and trimethylhexamethylene diisocyanate (experiments 26–31), respectively, as examples of the isocyanate compound according to the present invention.

In each experiment, use was made of 3.5 g carrier which was mixed with 100 ml of a TBT-solution (0.3–1.5 g TBT/100 ml CH$_2$Cl$_2$) and stirred for 1 hour. After decanting of said solution, the impregnated carrier was mixed with 100 ml of a diisocyanate solution (4–12 g diisocyanate/100 ml CH$_2$Cl$_2$) and stirred for 2 hours to bind said diisocyanate to the TBT-impregnated carrier. (In experiments 5–8 stirring was made for between 0.5 and 1 hour). After decanting of the solution, the carriers were dried under vacuum for 3 minutes in desiccator.

1.5 g of the dried carrier was then contacted with 100 ml of a urease solution and stirred for 1 hour to bind said urease to the isocyanate-treated carrier. The suspension was finally filtered over a net and washed 4 times with 100 ml of phosphate buffer solution and used for determination of activity. The following methods of determination were used.

A. Activity of bound urease

The urease treated carrier was stirred at 37° C. in 100 ml urea solution (250 mg/100 ml phosphate buffer, pH 7, 1/15 M, 5 ppm EDTA) for 1 hour. After 3 minutes and 1 hour, respectively, the converted amount of urea was determined according to the Berthelot-method. The results are given in Table 2 below.

B. Urease activity in the used solutions

The urease activity was determined in accordance with the prescriptions in H. U. Bergmeier, *Methoden der enzymatischen Analyse*, Vol. 1 (1974). The results are given in Table 2 below.

TABLE 2

| Experiment No. | Pretreatment of the carrier used cellulose g | Pretreatment of the carrier used TBT-solution g/100 ml | Pretreatment of the carrier used isocyanate-solution g/100 ml | reaction time TBT | reaction time isocyanate | Urease binding on 1.5 g carrier for 1 hour used amount U/100 ml | Urease binding on 1.5 g carrier for 1 hour actively bound |
|---|---|---|---|---|---|---|---|
| 5 | 3.5 g | 0.34 g | 4 g$^{(x)}$ | 1 h | ½ h | 1000 | 15 U |
| 6 | 3.5 g | 0.68 g | 4 g$^{(x)}$ | 1 h | ½ h | 1000 | 16 U |
| 7 | 3.5 g | 0.68 g | 4 g$^{(x)}$ | 1 h | 1 h | 1000 | 17 U |
| 8 | 3.5 g | 1.02 g | 4 g$^{(x)}$ | 1 h | 1 h | 1000 | 17 U |
| 9 | 3.5 g | 0.68 g | 4 g$^{(x)}$ | 1 h | 2 h | 1000 | 20 U |
| 10 | 3.5 g | 1.36 g | 4 g$^{(x)}$ | 1 h | 2 h | 1000 | 20 U |
| 11 | 3.5 g | 0.5 g | 1 g$^{(x)}$ | 1 h | 2 h | 1000 | 12.5 U |
| 12 | 3.5 g | 0.5 g | 2 g$^{(x)}$ | 1 h | 2 h | 1000 | 15.5 U |
| 13 | 3.5 g | 0.5 g | 6 g$^{(x)}$ | 1 h | 2 h | 1000 | 22.4 U |
| 14 | 3.5 g | 0.5 g | 8 g$^{(x)}$ | 1 h | 2 h | 1000 | 19.2 U |
| 15 | 3.5 g | 0.5 g | 10 g$^{(x)}$ | 1 h | 2 h | 1000 | 23.7 U |
| 16 | 3.5 g | 0.5 g | 12 g$^{(x)}$ | 1 h | 2 h | 1000 | 22.2 U |
| 17 | 3.5 g | 0.5 g | 6 g$^{(x)}$ | 1 h | 2 h | 1000 | 21.2 U |
| 18 | 3.5 g | 1.0 g | 6 g$^{(x)}$ | 1 h | 2 h | 1000 | 35.9 U |
| 19 | 3.5 g | 1.5 g | 6 g$^{(x)}$ | 1 h | 2 h | 1000 | 32 U |
| 20 | 3.5 g | 1.0 g | 6 g$^{(x)}$ | 1 h | 2 h | 1000 | 30 U |
| 21 | 3.5 g | 1.0 g | 8 g$^{(x)}$ | 1 h | 2 h | 1000 | 43.6 U |
| 22 | 3.5 g | 1.5 g | 10 g$^{(x)}$ | 1 h | 2 h | 1000 | 39.6 U |
| 23 | 3.5 g | 1.0 g | 8 g$^{(x)}$ | 1 h | ½ h | 50 | 18 U |
| 24 | 3.5 g | 1.0 g | 8 g$^{(x)}$ | 1 h | ½ h | 100 | 36.6 U |
| 25 | 3.5 g | 1.0 g | 8 g$^{(x)}$ | 1 h | ½ h | 500 | 40 U |
| 26 | 3.5 g | 1.0 g | 8 g$^{(xx)}$ | 1 h | 2 h | 50 | 11.3 U |
| 27 | 3.5 g | 1.0 g | 8 g$^{(xx)}$ | 1 h | 2 h | 100 | 10.1 U |
| 28 | 3.5 g | 1.0 g | 8 g$^{(xx)}$ | 1 h | 2 h | 200 | 13.6 U |

TABLE 2-continued

| Experiment No. | Pretreatment of the carrier used | | | reaction time | | Urease binding on 1.5 g carrier for 1 hour | |
|---|---|---|---|---|---|---|---|
| | cellulose g | TBT-solution g/100 ml | isocyanate-solution g/100 ml | TBT | isocyanate | used amount U/100 ml | actively bound |
| 29 | 3.5 g | 1.0 g | 4.4 g(xx) | 1 h | 2 h | 50 | 4.7 U |
| 30 | 3.5 g | 1.0 g | 4.4 g(xx) | 1 h | 2 h | 100 | 5.4 U |
| 31 | 3.5 g | 1.0 g | 4.4 g(xx) | 1 h | 2 h | 200 | 5.2 U |

(x)N,N',N''—tris(6-isocyanatohexyl)biuret
(xx)trimethylhexamethylene diisocyanate From Table 2, it is apparent that an increase of the binding capacity is achieved through increasing of the TBT-concentration from 0.34 g to 1 g TBT per 100 ml $CH_2Cl_2$. Furthermore, an increase of the binding capacity is achieved through extension of the reaction time for N,N',N''-tris(6-isocyanatohexyl)biuret. Under optimal conditions (for example, Experiment 21) 35-40 U of urease may be bound. Furthermore, under said optimal conditions, the amount of used urease (Experiments 23-25) could be lowered, while retaining high binding capacity.

To prevent possible activity losses, it may be suitable to add a phosphate buffer and EDTA in order to avoid deactivating the urease. Possible heavy metals in the used materials will thereby be complexed with said EDTA.

EXAMPLE 3

In this example Levasint is employed as a carrier for urease and for albumin. Levasint is a powder sold by Bayer AG and is a saponified ethylenevinylacetate-copolymer (ethylene-vinylalcohol-copolymer) having the following characteristics:

| | |
|---|---|
| range of melting | 105-180° C. |
| particle size | 80-200 um |
| sp. gravity | 0.97 g/cm$^3$ |
| absorption of water after 24 h at room temperature | 0.19% |
| after 30 days at room temperature | 0.30% |

Several separate samples of Levasint (2-4 g) were mixed with 100 ml of a TBT solution (1 g TBT in 100 ml $CH_2Cl_2$) and stirred for 1 hour. The TBT pretreated Levasint was mixed with 100 ml of an isocyanate solution (8 g N,N',N''-tris(6-isocyanatohexyl)biuret in 100 ml $CH_2Cl_2$) and stirred for 2 hours. After suction, this activated Levasint was washed twice each with 100 ml $CH_2Cl_2$. The activated Levasint was dried in vacuo for 0.5 hour in a desiccator.

The urease (Urease S sold by Boehringer, Mannheim) required for each batch was dissolved in 100 ml phosphate buffer solution (pH 7, 1/15 M, 5 ppm EDTA) and cross-linked with glutardialdehyde (GDA) at 0° C. (0.1 mg GDA/1000 U urease). The urease activity was determined by the Bergmeyer method mentioned above.

500 mg of the activated Levasint was mixed with 100 ml of the urease solutions of varying concentrations (see Table 3 below) and stirred for 1 hour. After suction, the urease-treated Levasint was washed 4 times with each 100 ml phosphate buffer solution.

A determination of activity of bound urease was then performed by the following procedure:

In Experiments 1.1, 1.2 and 1.3, the urease-coated Levasint was stirred for 1 hour at 37° C. in 300 ml urea solution (750 mg in 300 ml phosphate buffer, pH 7, 1/15 M, 5 ppm EDTA). From the amount of urea which was converted after 1 hour, the amount of bound active urease was determined (as determined by the Berthelot method). The value obtained at 37° C. was converted to the corresponding value at 25° C. with the factor of 0.66. The results are listed in Table 3 below.

In Experiments 2.1 and 2.2, the urease-coated Levasint was stirred at room temperature for 1 hour in 300 ml urea solution and the determination was carried out as described above for Experiments 1 and 2, but no factor was necessary. The results are also listed in Table 3 below.

Since Levasint W is hardly wetted and therefore only slightly influenced in aqueous solutions, it was furthermore attempted to hydrophilize this material through the influence of the tenside HB 509 (sold by Unilever Forschungs GmbH, Hamburg). Specifically, 50 g of Levasint W was stirred in 500 ml of a 0.2% solution of HB 509 in isopropanol and then left to stand for a longer time. After suction and drying, the pretreated Levasint was tested in the same way as described above. See Experiments 3.1 and 3.2 in Table 3 below.

In Experiments 4.1 and 4.2, 500 mg of the pretreated and activated carrier was stirred for 1 hour with 100 ml albumin solution (albumin from ox blood, Merck 12018, 5 mg% in phosphate buffer pH 7, 1/15 M, 5 ppm EDTA). After 1 hour, samples (2 ml each) were taken, filtered off and albumin determined directly in the filtrate.

After filtering, the albumin which was noncovalently bound to the carrier was determined in the filtrate joined with the wash solutions by Bio-Rad Protein assay with standards prepared from ox blood, Merck 12018. The carrier was treated as well with (a) phosphate buffer alone and (b) phosphate buffer which has been allowed to stand for 10 minutes with 5 ml of 6 m urea solution, in order to release any adsorptively bound albumin. The results are shown in Table 4 below.

TABLE 4

| Experiment No. | Albumin coating | | |
|---|---|---|---|
| | mg protein bound 500 mg carrier | Amount | |
| | | washed off with phosphate buffer | removed through urea-solution |
| 4.1 | 1.3 | 1.0 | — |
| 4.2 | 1.3 | — | 0.7 |

The results in Table 3 demonstrate that as the ratio of used activated carrier to urease concentration was varied, between 27 and 78% of the enzyme activity lost from the solution was found bound to the carrier.

The results in Table 4 also demonstrate that substantial amounts of albumin were adsorptively bound to the carrier. Such adsorptively bound albumin could be resolved through intensive washing.

TABLE 3

| Experiment No. | Used amount of urease U/100 ml | Loss of urea in initial solution U/500 mg carrier | Urease Coating Active urease U/500 mg carrier | % loss of urea | Protein bound mg/500 mg carrier |
|---|---|---|---|---|---|
| 1.1 | 344 | 127 | 47 | 37 | 0.1 |
| 1.2 | 344 | 152 | 57 | 37.5 | 0.2 |
| 1.3 | 344 | 93 | 32 | 34 | 0.4 |
| 2.1 | 400 | 186 | 97 | 52 | 0.7 |
|  | 837 | 172 | 82 | 48 | 0.9 |
| 2.2 | 110 | 67 | 52 | 78 | 0.3 |
|  | 277 | 142 | 68 | 48 | 0.7 |
|  | 656 | 209 | 86 | 41 | 0.9 |
| 3.1 | 120 | 101 | 54 | 53 | 0.5 |
|  | 558 | 234 | 63 | 27 | 1.3 |
| 3.2 | 130 | 110 | 45 | 41 | 0.2 |
|  | 328 | 152 | 65 | 43 | 0.5 |
|  | 632 | 193 | 76 | 39 | 0.8 |

In summary, the results in this examples demonstrate that a binding of proteins such as urease or albumin to this synthetic carrier is possible. The binding is not only covalent; on a hydrophobic substrate also adsorption is contributing. In comparison to a Cuprophan ® membrane, the covalently bound portion is substantially smaller with Levasint, since the portion of free hydroxylgroups of Levasint probably is much smaller. Also, the hydroxylgroups in the ethylene-vinylalcohol-copolymer are slowly reactive secondary alcohol groups.

Since enzyme activity could be redissolved partially from the carrier through washing, the binding on the synthetic copolymer is also ascribed to interactions with the hydrophobic polyethylene areas.

A further characteristic of the Levasint carrier is that it is hardly wettable and, as a consequence of the specific gravity of 0.97 g/cm$^2$, that it tends to float on the surface in aqueous solution. Therefore, a substrate as e.g. cellulose is preferred.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A method of binding a biologically active material to a carrier containing hydroxyl groups, said method comprising the steps of reacting a sufficient amount of an isocyanate compound with said carrier in the presence of an orthotitanium acid ester which catalyzes the formation of urethane bonds to form an isocyanate-containing carrier; and binding said biologically active material to the isocyanate-containing carrier.

2. A method of binding a biologically active material to a carrier containing hydroxyl groups, said method comprising the steps of reacting a sufficient amount of an isocyanate compound with said carrier in the presence of a non-toxic titanium based compound which catalyzes the formation of urethane bonds to form an isocyanate-containing carrier; treating the isocyanate-containing carrier to remove therefrom titanium based compound; and binding said biologically active material to the isocyanate-containing carrier.

3. A method according to claim 2, wherein said non-toxic titanium based compound catalyzing the formation of urethane bonds is an orthotitanium acid ester.

4. A method according to claim 1 or 2, wherein said orthotitanium acid ester is an ester containing low molecular weight alkyl groups.

5. A method according to claim 4, wherein said low molecular weight alkyl groups are selected from methyl, ethyl, n-propyl, i-propyl, n-butyl and isomers and mixtures thereof.

6. A method according to claim 1 or 2, wherein said urethane forming catalyst is tetrabutyltitanate.

7. A method according to claim 1 or 2 wherein said isocyanate compound is selected from diisocyanates, triisocyanates, polyisocyanates and prepolymers formed thereof.

8. A method according to claim 7, wherein said isocyanate compound is a triisocyanate, said carrier is cellulose, and said biologically active material is urease.

9. A method according to claim 8, wherein said isocyanate compound is selected from hexamethylene diisocyanate, trimethylhexamethylene diisocyanate and N,N',N''-tris(6-isocyanatohexyl)biuret.

10. A method according to claim 8, wherein said isocyanate compound is dissolved in a solvent selected from dichloromethane, ether, acetone and frigen.

11. A method according to claim 10, wherein said isocyanate solution contains about 1 to about 24 g isocyanate compound per 100 ml of said solution.

12. A method according to claim 7, wherein said non-toxic titanium based compound catalyzing the formation of urethane bonds is in the form of a solution of an orthotitanium acid ester in a solvent selected from ether, dichloromethane, acetone and frigen.

13. A method according to claim 12, wherein said orthotitanium acid ester solution is a solution containing between about 0.3 and about 1.5 g tetrabutyltitanate per 100 ml dichloromethane.

* * * * *